(12) United States Patent
Kato et al.

(10) Patent No.: US 6,268,157 B1
(45) Date of Patent: Jul. 31, 2001

(54) METHOD OF SCREENING FOR PHARMACEUTICALS BY DETECTING CROSS TALK BETWEEN INTRACELLULAR SIGNALS AND INTRANUCLEAR RECEPTORS

(75) Inventors: Shigeaki Kato, Saitama; Jun Yanagisawa, Tokyo, both of (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/188,884

(22) Filed: Nov. 10, 1998

(30) Foreign Application Priority Data

Jan. 14, 1998 (JP) .................................. 10-017818

(51) Int. Cl.[7] .......................... G01N 33/53; C12N 15/12; C12N 15/63; C12N 5/00; C07K 1/00

(52) U.S. Cl. ...................... 435/7.1; 435/69.1; 435/252.3; 435/320.1; 435/325; 530/351

(58) Field of Search .................................... 435/7.1, 69.1, 435/325, 320.1, 252.3; 530/351

(56) References Cited

FOREIGN PATENT DOCUMENTS

WO 95/30900    11/1995  (WO) .

OTHER PUBLICATIONS

Massague et al. Trends in Cell Biology, vol. 7, pp. 187–192, May 1997.*

Yanagisawa et al., Feb. 26, 1999, "Convergence of Transforming Growth Factor–β and Vitamin D Signaling Pathways on SMAD Transcriptional Coactivators" *Science*, vol. 283, No. 5406, pp. 1317–1321.

Erica A. Golemis, Ilya Serebriiskii, Jeno Gyuris, & Roger Brent; Current Protocols in Molecular Biology (1997); "Analysis of Protein Interactions"; pp. 20.0–20.1.3; John Wiley & Sons, Inc.

Clontech Laboratories, Inc. Palo Alto, CA; "Mammalian Matchmaker Two–Hybrid Assay Kit"; User Manual, (PT3002–1); Catalog #K1602–1; pp. 7–13.

Jeno Gyuris, Erica Golemis, Helen Chertkov & Rober Brent; "Cdi1, a Human G1 and S Phase Protein Phosphatase that Associates with Cdk2"; Cell, Nov. 19, 1993, vol. 75, pp. 791–803.

Roger Brent and Mark Ptashne; "A Eukaryotic Transcriptional Activator Bearing the DNA Specificity of a Prokaryotic Repressor"; Cell; Dec. 1985 (Part 2); vol. 43, pp. 729–736.

Erica A. Golemis & Robert Brent; "Fused Protein Domains Inhibit DNA Binding by LexA"; Molecular and Cellular Biology; Jul. 1992, pp. 3006–3014; vol. 12, No. 7.

Edward Giniger, Susan M. Varnum & Mark Ptashne; "Specific DNA Binding of GAL4, A Positive Regulatory Protein of Yeast"; Cell, vol. 40; Apr. 1985, pp. 767–774.

(List continued on next page.)

*Primary Examiner*—Prema Mertz
*Assistant Examiner*—Joseph F. Murphy
(74) *Attorney, Agent, or Firm*—Morgan, Lewis & Bockius LLP

(57) ABSTRACT

Under the knowledge which two kinds of intracellular signal transfer mechanism of TGF-β super family receptor exist: a pathway via Smad molecule and a pathway via novel MAP kinase such as TAB1 and TAKI, and the knowledge of interaction of Smad molecule with intranuclear receptor or CBP/p300 on the transcription control by Smad molecule, a screening method and a molecular designing method for pharmaceuticals with identified site of action and higher specificity can be accomplished.

8 Claims, 7 Drawing Sheets

OTHER PUBLICATIONS

Alan G. Hinnebusch; "Evidence for Translational Regulation of the Activator of General Amino Acid Control in Yeast"; Proc. Natl. Acad. Sci., USA; vol. 81; Oct. 1984, pp. 6442–6446.

Steven J. Triezenberg, Robert C. Kingsbury, & Steven L. McKnight; "Functional Dissection of VP16, the Transactivator of Herpes Simplex Virus Immediate Early Gene Expression"; Genes & Development, Cold Spring Harbor Laboratory, 1988, pp. 2:718–729.

Garry P. Nolan, Sankar Ghosh, Hsiou–Chi Liou, Paul Tempst, & David Baltimore; "DNA Binding and IKB Inhibition of the Cloned p65 Subunit of NF–KB, a rel–Related Polypeptide"; Cell, vol. 64, Mar. 8, 1991, pp. 961–969.

Richard A. Sturm, Gokul Das, & Winship Herr; "The Ubiquitous Octamer–Binding Protein Oct–1 Contains a POU Domain with a Homeo Box Subdomain"; Genes & Development, Cold Spring Harbor Laboratory, 1988, pp. 2:1582–1599.

Rosemary Watt, Lawrence W. Stanton, Kenneth B. Marcu, Robert C. Gallo, Carlo M. Croce, & Giovanni Rovera; "Nucleotide Sequence of Cloned cDNA of Human c–myc Oncogene"; Nature, vol. 303, Jun. 23, 1983, pp. 725–728.

Peter Angel, Kazue Hattori, Tod Smeal, & Michael Karin; "The Jun Proto–Oncogene is Positively Autoregulated by Its Product, Jun/AP–1"; Cell, vol. 55, Dec. 2, 1988, pp. 875–885.

Woodring E. Wright, David A. Sassoon, & Victor K. Lin; "Myogenin, A Factor Regulating Myogenesis, Has a Domain Homologous to MyoD"; Cell, vol. 56, Feb. 24, 1989, pp. 607–617.

Istvan Mucsi and Howard J. Goldberg; "Dominant–Negative SMAD–3 Interferes with Transcriptional Activation by Multiple Agonists"; Biochemical and Biophysical Research Communications, vol. 232; Article No. RC976321; 1997, pp. 517–521.

Chumakov, P.M., Genetika, 1988, 24:602–612.

* cited by examiner

METHOD OF SCREENING FOR PHARMACEUTICALS BY DETECTING CROSS TALK BETWEEN INTRACELLULAR SIGNALS AND INTRANUCLEAR RECEPTORS

BACKGROUND OF THE INVENTION

1. Field of the invention

This invention relates to a method for screening and molecular designing pharmaceuticals useful for various diseases on bone, cartilage, liver, kidney, skin, immune system, central system and the like, or benign tumor, malignant tumor, hyperplasia, fibrosis and the like.

2. Related Background Art

It has been attempted to develop TGF-β super family molecule itself, or antagonist or agonist thereof as a pharmaceutical based on focusing the function of TGF-β super family, and some pharmaceutical screening methods therefor have been proposed.

For example, (1) as a method for screening by using cell system, there are screening methods for agonist or antagonist by using the activity of TGF-β super family in growing, differentiating, killing or maintaining animal cells as an indicator. Those methods are, for example, (i) a screening method using inhibition activity of TGF-β on the growth of a tumor cell, or propagation accelerating activity of it on the growth of another tumor cell as an indicator, (ii) a screening method focusing on the immuno suppression activity of TGF-β and (iii) a screening method focusing on production accelerating effect on extracellular matrix by TGF-β. Furthermore, (2) a screening method focusing on the interaction between TGF-β super family and TGF-β receptor super family is known.

However, it is known that TGF-β super family has significantly wide-ranging functions, and thus, a mere agonist or antagonist for TGF-β super family may have a problem such that main function and side function can not be sufficiently differentiated, and consequently they are not sufficient for a screeningmethod for pharmaceuticals. That is, the above screening method can not differentiate only main function from other functions, and very likely screen materials with low specificity not to be an candidate for pharmaceuticals. Furthermore, even if a useful candidate for pharmaceuticals could be screened, it still remains difficulty to find guideline for synthesizing a useful derivatives and to do molecular designing.

SUMMARY OF THE INVENTION

An object of the present invention is to provide a novel method for screening pharmaceuticals, which overcomes the above prior art's problems.

As a result of intensive efforts to overcome the above-mentioned problems, the present inventor succeeded to develop a screening method for pharmaceuticals (inhibitor, accelerator etc.) with more specificity and a method for molecular designing them, based on a novel principle by focusing on intracellular signal transfer mechanism of TGF-β receptor super family, and accomplished this invention.

Although a pathway via Smad molecule and the MAP kinase pathway via TAB1, TAK1 and the like have been known as an intracellular transfer mechanism of TGF-β receptor super family, it is little understood how the expression of the targeted gene is finally controlled by these pathways. Especially, it is known that Smad molecule affects to transcription control in nucleus, but a transcription control factor interacted with Smad molecule in higher animal cell has not been determined.

The present inventor demonstrated that the interaction among Smad molecule, intranuclear receptor and transcription coupling factor is important physiologically in the transcription control mechanism of Smad molecule. Under the above-mentioned knowledge, the present inventor developed a method for screening and a method for molecular designing pharmaceuticals based on the novel principle which focuses on the transcription control mechanism via the intracellular signal transfer mechanism of TGF-β receptor super family.

In the signal transfer pathway of Smad, as a pharmacofunction being presumable from the prior art, there are (i) phosphorylation into Smad 2, 3 and the like (obtaining transition ability into nucleus), (ii) dimer formation of Smad molecule, and (iii) discovering of inhibitor against the signal transfer pathway such as Smad 6, 7, or controlling of function of the pathway. However, because these pharmacofunctions are appeared in cytoplasm but not in ucleus and the pathway is well conserved, a screening method for pharmaceuticals based on such functions is not suitable to search pharmaceuticals with high specificity. Furthermore, other than the above (ii), the concrete interaction between molecules has not been clarified, and thus a theoretical approach for molecular designing based on the structure is not appropriate.

On the other hand, in connection with the transcription control by Smad molecule, the present inventor obtained the knowledge about the interaction of Smad molecule with intranuclear receptor or CBP/p300, thereby clarified a tangible partner of Smad. According to such knowledge, the present inventor developed a screening method for pharmaceuticals with specified site of action and high specificity. By using the above method, it becomes possible to find useful pharmaceutical candidates and to provide a guideline or molecular designing for synthesizing more useful materials. Based on such knowledge, pharmaceutical designing becomes possible. Various kinds of known techniques to determine the three dimensional structure such as X-ray crystallographic structure analysis, spectroscopic analysis such as NMR (nuclear magnetic resonance), IR(Infrared), and CD(circular dichroism), or various biological modification such as a point mutation techniques can reveal the three dimensional structure of the binding site of a Smad molecule and intranulcear receptor and transcription coupling factor. Thus obtained three dimensional structural data can be used to design pharmaceuticals, if necessary with a numerical calculating method such as a commercially available molecular modeling computer softwares (SYBYL (Tripos Inc.,St.Louis,USA); InsightII/Discover(Molecular Simulations Inc., San Diego, USA);Quanta/CHARMM (Molecular Simulations Inc., San Diego, USA);LOOK (Molecular Applications Group, Palo Alto, USA);CAChe (Oxford Molecular Group, Oxford, UK).

Furthermore, base on the above principle, it becomes possible to develop a screening method for an agonist or an antagonist of intranuclear receptor (for example, vitamin D receptor) with higher specificity. Since intranuclear receptors are distributed over various tissues, it is impossible to avoid some side effect of agonist or antagonist type pharmaceuticals screened by the prior method, which such intranuclear receptors are simply targeted. However, upon focusing on the interaction between Smad molecule and intranuclear receptors, according to the present invention, it is possible to inhibit or accelerate only the specific transcription control using Smad as a transcription coupling factor. Therefore, it becomes possible to search excellent pharmaceuticals with good efficiency and specificity (targeting various disease of bone, skin, liver, kidney, immune system, center system and the like, or benign tumor, malignant tumor, hyperplasia or fibrolysis) in addition to the known usefulness of intranuclear receptor agonist or antagonist.

In other words, the present invention provides a method to develop a novel therapeutic agent based on the novel knowledge of the interaction of Smad molecule with intranuclear receptor or with CBP/p300.

The present invention will be more fully understood from the detailed description given hereinbelow and the accompanying drawings, which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
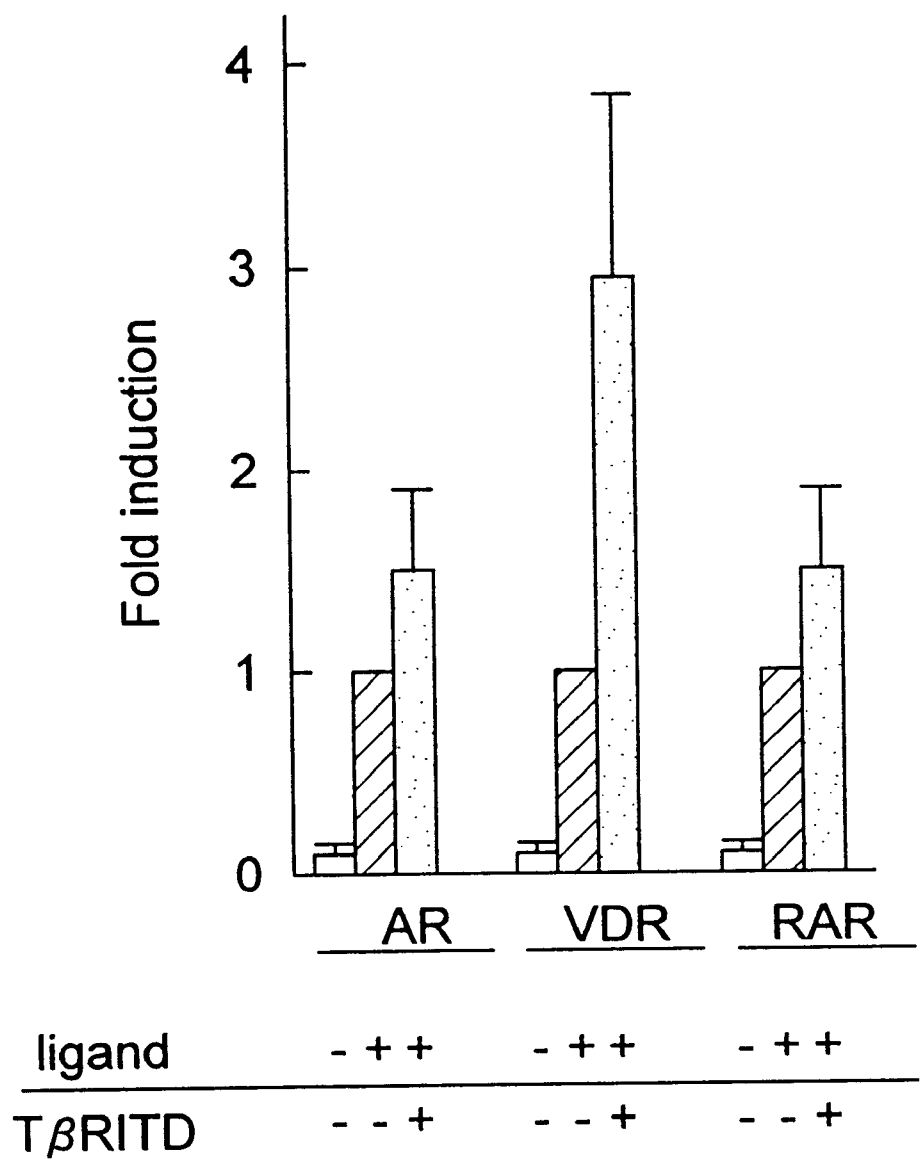
FIG. 1 is a diagram showing the results of Example 1.

This invention will be hereinafter explained in detail along with some embodiments.

A battery of factors belonging to TGF-β super family such as TGF-β and BMP show various physiological functions and they act as aggravation factor or amelioration factor invariousdiseaseofbone, cartilage, liver, kidney, skin, immune system and the like or carcinoma. On the other hand, functions via vitamin D3, retinoic acid, steroid hormone and receptors thereof (intranuclear receptor/steroid hormone receptor super family) are also various, and target tissues thereof are overlapped those of the above TGFβ super family.

The present inventor found that the intracellular signal of TGF-β affects the transcription control of intranuclear receptors, that such function is expressed via intracellular signal transfer molecule of TGF-β, Smad, and that Smad3 affects particularly to transcription activity of VDR as transcription coupling factor and intermediates the interaction between VDR and CBP/p300.

Furthermore, the present inventor found that Smad3 directly binds to CBP/p300 which is thought to be indispensable to activation of almost all intranuclear receptors, and thereby elucidated the cross-talk at molecular level between TGF-β intracellular signal and wide-ranging intranuclear receptor transcription control.

Upon elucidation of the cross-talk between TGF-β intracellular signal and intranuclear receptor transcription control, an entirely different approach to create therapeutic agent involving TGF-β and intranuclear receptor, especially VDR becomes possible.

In other words, a pharmaceutical agent affecting intracellular signal of TGF-β and intranuclear receptor transcription activity improves tissue specificity and efficiency, which have not been accomplished heretofore. And the pharmaceutical agent enables to establish various kind of screening system based on molecular interaction. Thus, materials found by the screening method based on such knowledge include effective therapeutic agents for diseases of bone, cartilage, liver, kidney, skin, immune system and central system, or benign tumor or malignant tumor, hyperplasy, fibrosis and the like.

While TGF-β employs Smad2 or 3 and Smad4 for intracellular signal transfer, BMP belonging to TGF-β super family employs Smadl and Smad4 having similar structure for intracellular signal transfer. The present invention provides a novel screening method using mainly TGF-β, Smad3, CBP/p300 and various intracellualr receptors, but it can be easily assumed to be common to BMP and Smadl.

Because Smad3 binds to CBP/p300 directly, this invention is also applicable to screening of transcription activity control materials of transcription activating factors (CREBP, AP-1 and the like) other than intranuclear receptors.

The screening method of this invention will be exemplified.

Screening Method (I):

Based on the knowledge found by the present inventor, it is possible to screen cross talk between intracellular signal from TGF-β family receptors and intranuclear receptors and to screen (search) materials affecting the cross talk (see Example 1).

Screening Method (II):

A screening method is possible by using the Two-Hybrid System(Gyuris, J., Cell, 1993,75:791–803; Golemis, E. A., Current Protocols in Molecular Biology [John Wiley & Sons, Inc.], 1996, Ch. 20.0 and 20.1). In order to screen materials affecting the interaction (binding) between intranuclear receptor and Smad molecule, the Two-Hybrid System can be used.

As a transcription activating domain used for the Two-Hybrid System,for example, GAL4 transcription activating domain (Brent, R., Cell,1985, 43: 729–736), [Bicoid], [c-Fos], [c-myc], [v-Myc], [B6], [B7], [B42] (Golemis, A. E., Mol. Cell Biol., 1992,12:3006–3014) or [VP16] (CLONTECH Corp., Mammalian MATCHMAKER Two-Hybrid Assay Kit) may be listed.

A DNA binding domain used for the Two-Hybrid System, for example is identified in transcription factors such as GAL4 (Giniger, E., Cell, 1985,40: 767–774) p53 (Chumakov, P. M.,Genetika, 1988,24:602–612), GCN4 (Hinnenbush, A. G., Proc. Natl. Acad. Sci., 1984, 81: 6442–6446), VP16 (Triezeneberg, S. J., Genes. Dev., 1988, 2: 718–729) ReloA (Nolan, G. P., Cell, 1991, 64: 961–969) Oct-1 (Strum, R. A., Genes. Dev., 1988, 2: 1582–1599) c-Myc (Watt, R., Nature, 1983, 303:725–728), c-Jun (Angel, P., Cell, 1988, 55: 875–885), MyoD (Write, W. E., Cell, 1989, 56: 607–617).

The principle to screen materials affecting the binding between proteins A and B by using the Two-Hybrid System is explained hereinbelow. An expression vector for the fusion protein of the above-mentioned transcription activating domain and the protein A, an expression vector for the fusion protein of the above-mentioned DNA binding domain and the protein B, and an eucaryotic host having an expression unit comprising an appropriate reporter gene in its nucleus are prepared. The reporter gene is constructed as an expression unit consisting of promoter region which is activated when both fusion proteins bind together and the reporter gene linked to the promoter region at the downstream of the region.

It is possible to screen materials affecting the binding of proteins A and B by detecting the expression of the reporter gene and selecting a material affecting the amount of the expression.

An example of the expression vector may be used any expression vector without any restriction as long as it can stably express proteins coded by (1) fusion DNA fused with DNA coding the above-mentioned transcription activating domain and an intranuclear receptors or Smad, and (2) fusion DNA fused with DNA coding the above-mentioned DNA binding domain and an intranuclear receptor or Smad in eucaryote hosts. An example of intranuclear receptor is preferably VDR, but other intranuclear receptor/hormone receptors, such as RARAα, β, γ, RXRα, β, γ, PPARα, β, γ, ER, AR, PgR, GR and the like may be used without any restriction. Any DNA coding an intranuclear receptor may be used as long as it includes DNA coding ligand/hormone binding domain. An example of Smad molecule is preferably Smad3, but DNA coding Smad2 or other molecules belonging to Smad family may be used without any restriction.

Any expression vector for reporter gene may be used as long as it includes the promoter region activated upon the binding of the both fusion proteins and reporter gene linked to the promoter region at the downstream of the gene and can express the reporter gene products specifically and efficiently when the both fusion proteins bind together (see Example 2).

Screening Method (III):

A screening method is possible by employing antigen antibody reaction. After Smad molecules and intranuclear receptors are expressed in cells and those cells are cultivated with a material to be tested for a certain period, cells are crushed to prepare cell lysate. Effect of the material to be tested against the interaction (binding) of both molecules (Smad-intranuclear receptor) can be detected by immune precipitation with antibody against one of those molecules, and detecting or quantifying another molecule involved in the immune precipitate with a immunological technique. The screening for materials inducing the binding of the both molecules is easily accomplished by adding a material to be tested alone to the above-mentioned culture system and performing the above-mentioned experiments, and then comparing to the immune precipitate obtained from cells without the material. Material modifying (accelerating or suppressing) or inhibiting the binding of the both molecules can be screened by adding an appropriate agonist/hormone of an intranuclear receptor and a material to be tested to the above-mentioned culture system simultaneously and performing the above described experiments, and then by comparing to immune precipitate obtained from cells without the material.

Smad and intranuclear receptors may be used by expressing as a fusion protein fused with tag such as FLAG-, HA-, His-, Fc portion of immunoglobulin, GST-, GFP or labeled protein/ peptide. In such case, an antibody used for immune precipitate or immunological detection may be an antibody recognizing those tags. Instead of immune precipitation with an antibody, the targeted protein complex can be captured by using Ni or glutathione immobilized on a solid surface such as beads. Furthermore, in order to detect the targeted protein, by using the feature of the fusion tag/labeled protein/ peptide, it is possible to detect the targeted protein based on its enzyme activity and fluorescence activity. As the intranuclear receptor, a ligand binding domain alone, or any fusion protein including a ligand binding domain can be used.

When the targeted protein in the Smad—intranuclear receptor complex obtained by immune precipitate or the above-mentioned method is to be detected or quantified, separation by SDS-polyacrylamide gel electrophoresis and detection by a western blotting can be used. ELISA or RIA can be also used to quantify it.

As a simple laboratory procedure, it is possible to immobilize an antibody which recognizes one of the fusion protein molecules or the fusion protein itself, Ni, glutathione and the like on ELISA plate or beads, to capture Smad— intranuclear receptor complex from the above-mentioned cell lysate, and to detect or quantify the targeted protein molecule in the captured complex by using an antibody recognizing another protein molecule. For example, like commonly used in detection procedures, a direct assay using an antibody labeled with an enzyme or radioisotope, an indirect assay using labeled secondary antibody, or an biotin-avidin assay which uses biotin-labeled antibody and quantifies with labeled avidin can be used. Where one of the protein molecules is expressed as a fusion protein with fluorescence proteinsuchas GFP, the interaction (binding condition) of Smad and intranuclear receptor can be determined by measuring the fluorescence directly after capturing Smad—intranuclear complex on solid surface with for example an antibody recognizing another protein molecule (see Example 3).

Screening Method (IV):

Based on the interaction of Smad and intranuclear receptors, materials affecting the interaction can be screened in cell-free system (see Example 4).

Screening method (V):

A screening can be done by detecting the interaction of transcription coupling factor and Smad molecule. CBP and P300 act as a transcription coupling factor mediating transcription activity from many transcription control factors including intranuclear receptors. VDR does not bind CBP/ P300 directly. However it is demonstrated that VDR binds CBP/P300 via Smad3 as described below.

Consequently, it is necessary to sufficiently consider functions over the binding of Smad molecule and CBP/P300 in order to screen materials affecting the transcription control by Smad molecule and intranuclear receptor. Thus, a screening system for materials affecting the binding Smad molecule and CBP/p300 can be established by applying the following examples.

The experimental result using dominant negative Smad3 suggests that Smad3 accelerates transcription control by cAMP, phorbol ester or PDGF (Istvan Mucsi, et al., BBRC, 232, 517–521, 1997). However, since the mechanism has not been demonstrated, it has been difficult to screen materials modifying such wide-ranging functions of Smad3. The present invention makes such wide-ranging functions via Smad3 understandable systematically as the interaction of Smad molecule and CBP/p300. Consequently, it becomes possible to develop a screening system for materials affecting the binding of the above-mentioned both molecules.

An example of such screening method is described below. The method uses GST-pull down method (described supra)

employing GST-Smad fusion molecule and labeled CBP/p300, and can detect materials modifying the binding of the both molecules by adding a material to the reaction system upon reaction of the both molecules. Also, GST-pull down method employing GST-CBP and GST-p300 fusion protein and labeled Smad molecule can be used.

Any system which can measure the interaction (binding) between proteins other than GST-pull down method described above enables to screen materials accelerating or suppressing the interaction of Smad molecule and CBP/p300. Such system includes both cell and cell-free system, and can use easily ELISA, RIA, SPA method, BIACORETM, fluorescence polarization method, and the Two-Hybrid System. A partial peptide of Smad molecule or CBP/p300 molecule can be used. Such partial peptide of Smad or CBP/p300 molecule can be used as a fusion protein fused with tag such as FLAG-, HA-, His-, Fc portion of immunoglobulin, GST-, GFP or labeled protein/peptide.

EXAMPLE

This invention will be hereinbelow explained in detail by some examples. However, this invention is not limited by the following examples. The contents of Application No.10-17818, filed Jan. 14, 1998, in Japan is hereby incorporated by reference.

Example 1

TbetaR-I TD in which a gene coding constructively active modified TGF-β type I receptor (TβRI-TD) was introduce into higher animal expression vector was used to introduce TGF-β signal into cells constructively.

The gene coding androgen receptor (AR), the gene coding vitamin D3 receptor (VDR), or the gene coding retinoic acid receptor (RAR) were introduced into higher animal expression vector pSG5, respectively, and each expression plasmids for respective receptors was constructed (pSG5-AR, pSG5-VD or pSG5-RAR), and those plasmids were used in the following experiments. Plasmid with only each expression vector was used as control.

Reporter gene expression plasmid was used in which the sequence corresponding to each hormone receptor/intranuclear receptor was inserted into CAT reporter gene expression vector.

COS-1 cells which were cultured in Dulbeccols modified Eagle's medium-5% dextran-coated activated charcoal treated fetal calf serum without phenol red were used for the following experiments. COS-1 cells were cultivated in a 10 cm diameter Petri dish. At the point that cells saturation density was reached to 40–50%, the cells were combined with above-mentioned plasmids according to each purpose to make 20 μg in total, and the plasmids were introduced into cells by calcium coprecipitation method. As a internal reference, 3 μg of the expression vector pCH110 (Pharmacia) of β-galactosidase gene was introduced into cells simultaneously, and the introduction efficiency among respective Petri dishes was adjusted based on the amount of expression of the gene. Each matrial to be tested such as testosterone, 1,25(OH)2VD3 and retinoic acid was added into Petri dish one hour after the gene introduction, and thereafter was also added upon medium exchange.

Twenty-four hours after the gene introduction, cells were washed with fresh culture medium and continued to be cultured for additional 24 hours. Cells were crushed with freeze and thaw method to prepare cell extract. CAT activity was measured and concurrently β-garactosidase activity were measured to adjust the data.

The result showed that the transcription activity made by the addition of testosterone or retinoic acid via AR or RAR was slightly reinforced by signal from TGF-β. The transcription activity made by the addition of 1,25(OH)2VD3 via VDR was significantly reinforced by signal from TGF-β (FIG. 1). These results demonstrate that intracellular signal of TGF-β affects (reinforces) transcription activity of hormone receptor/intranuclear receptor.

Accordingly, by using this analysis system, it is possible to screen materials affecting transcription control mechanism of hormone receptor/intranuclear receptor mediated by intracellular signal of TGF-β.

In other words, it is possible to screen hormone agonist or antagonist which have different dependency on TGF-β signal—intranuclear receptor interaction by the method which comprises addition of any various material to be tested into the system instead of physiological ligands such as testosterone, 1,25(OH)2VD3 or retinoic acid, or together with them in the presence or absence of signal of TGF-β and comparison the transcription activity of each receptor. It is likewise possible to screen accelerator or inhibitor of TGF-β signal—intranuclear interaction.

Example 2 Two-hybrid analysis using higher animal cells

COS-1 cells which were cultured in Dulbecco's modified Eagle's medium—5% dextran-coated activated charcoal treated fetal calf serum without phenol red were used for the following experiments. COS-1 cells were cultivated in a 10 cm diameter Petri dish. At the point that cell saturation density was reached to 40–50%, 20 μg of the following plasmid in total was introduced into cells by calcium coprecipitation method. As a internal reference, 3 μg of the expression vector pCH110 (Pharmacia) of β-galactosidase gene was introduced simultaneously, and introduction efficiency among respective Petri dishes was adjusted based on the amount of the expression of the gene. Each material to be tested such as VD3 was added into Petri dish one hour after the gene introduction, and thereafter was also added upon medium exchange. Twenty-four hours after the gene introduction, cells were washed with fresh culture medium and continued to be cultured for additional 24 hours. Cells were crushed with freeze and thaw method to prepare cell extract. CAT activity was measured and β-garactosidase activity was measured concurrently to adjust the resulting data.

As a plasmid for the two-hybrid analysis, the gene coding D,E,F domains of VDR was introduced into pM(Clontech) vector and thereby the expression plasmid of GAL4 DNA-binding domain—VDR(DEF) fusion protein was constructed. Also, genes coding Smad2 and 3 were introduced into pVP16(Clontech) vector and those were used as expression plasmid for VP16—Smad2 or VP16—Smad3 fusion proteins. As a reporter gene expression plasmid, 17M5CAT in which CAT gene was inserted into 17M5 (including 5 times of USA 17 mer of GAL-4 recognition site). These expression plasmids were introduced into COS-1 cells as described in above.

Figure 2:
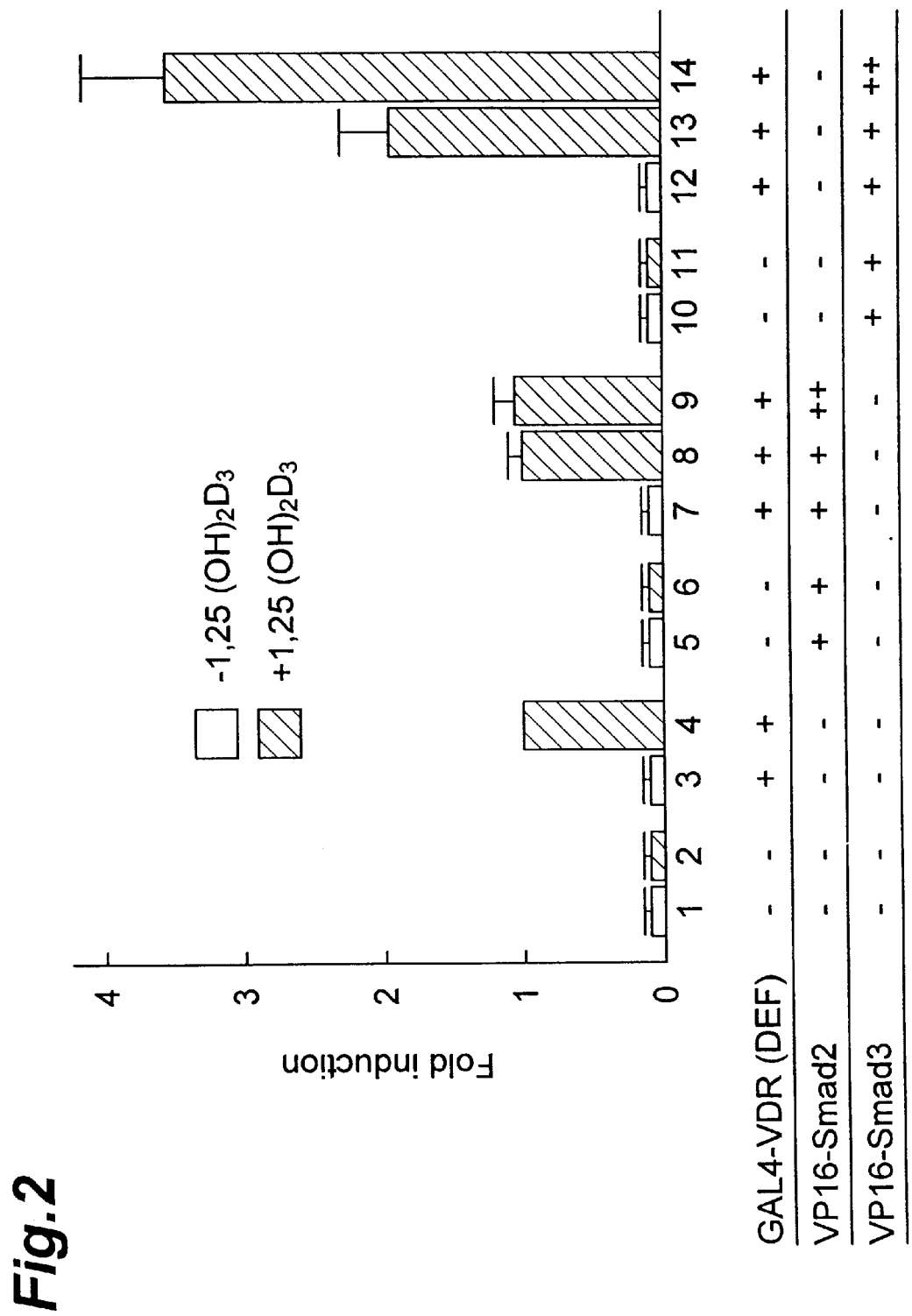
FIG. 2 is a diagram showing the results of Example 2.

In cells which expressed GAL4 DNA-binding domain—VDR(DEF) and VP-16-Smad2 or GAL4 DNA-binding domain—VDR(DEF) and VP-16-Smad3, stronger CAT activity increase was detected in the presence of 1 nM of 1α, 25(OH)2VD3, compared with that in the absence of 1α, 25(OH)2VD3 (see FIG. 2). It was shown that Smad3 and VDR bonds each other in the presence of 1α, 25(OH)2VD3.

By using this analysis system, it is possible to screen materials reinforcing the interaction of Smad3 and VDR. It is also possible to screen materials inhibiting the binding of Smad2 or Smad3 and VDR recognized in the presence of VD3 agonist such as 1,25(OH)2VD3.

Example 3
Immune Precipitate Method—immunoblotting Method

The following two kinds of expression plasmids were introduced into COS-1 cells by the same procedure as set forth Example 1. One hour after the gene introduction, 1,25(OH)2VD3 was added into Petri dish to be 1 nM at its concentration or not added (for comparison), and thereafter was also added at same concentration upon medium exchange. Twenty-four hours after the gene introduction, cells were washed with fresh culture medium and continued to be cultured for additional 24 hours. (1) pSG5-VDR in which VDR gene is inserted into higher animal expression vector pSG5, and (2) the plasmid in which FLAG-tagged Smad3 gene is inserted into higher animal expression vector pcDNA3 (Invitrogen) were used. After lysing cells, immune precipitation was done with anti-FLAG monoclonal antibody M2 (IBI; Eastman Kodak). Then, coprecipitated proteins were separated by 8% SDS-polyacrylamide gel electrophoresis. Separated proteins were transferred onto PVDF membrane (Bio-Rad), and then VDR was detected by using rabbit anti VDR antibody and alkaline phosphatase labeled anti rabbit IgG antibody (Promega).

Figure 3:
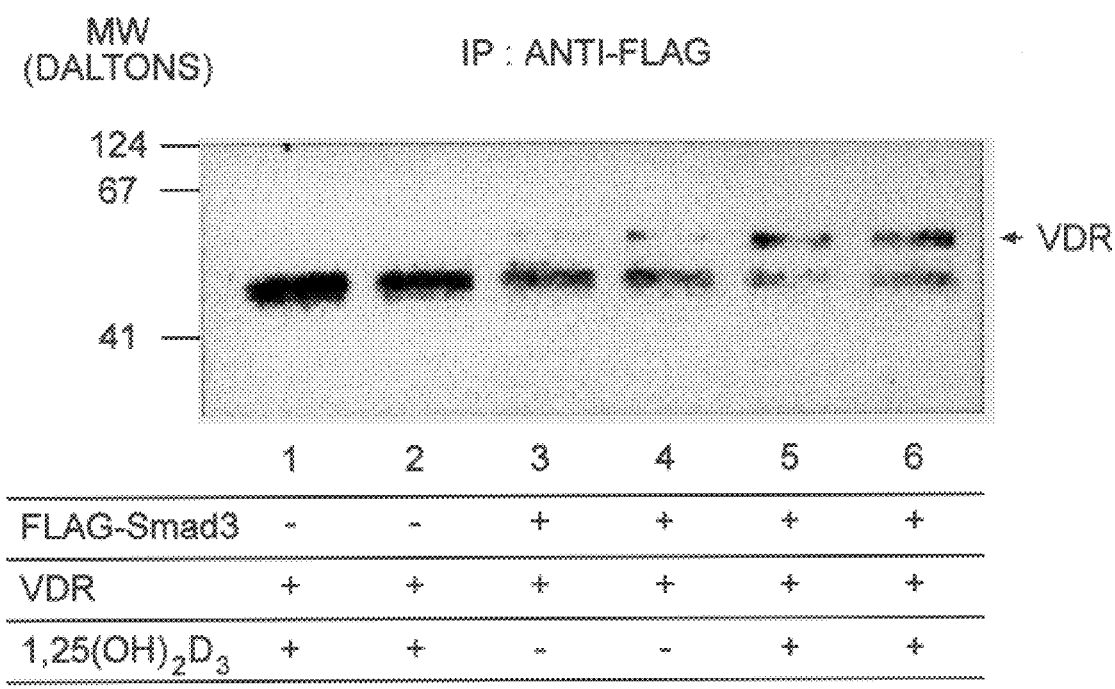
FIG. 3 is electrophoresis patterns showing the results of Example 3.

The results show that VDR was barely detected in the example using cells without 1,25(OH)2VD3. On the other hand, the VDR band was clearly detected in the example using cells added with 1,25(OH)2VD3 (FIG. 3).

By using this analysis system, it is possible to screen materials accelerating the interaction (binding) of Smad3 and VDR. Furthermore, it is possible to screen materials inhibiting the interaction (binding) of Smad3 and VDR in the presence of agonist such as 1,25(OH)2VD3 by adding any materials into this culture system.

Example 4
Detection System for Interaction of CDR and Smad Molecule
—GST-pull Down Analysis—

Figure 4:
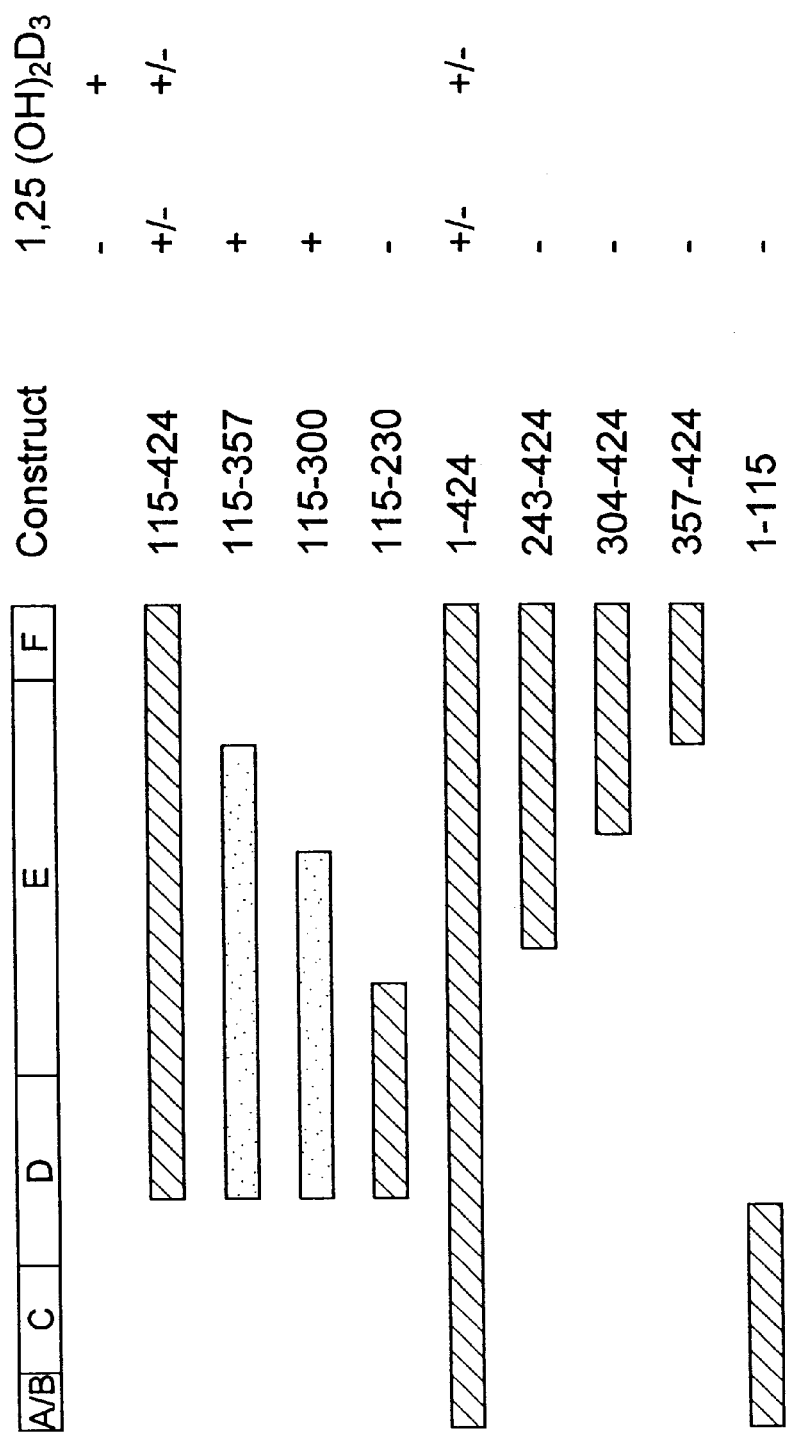
FIG. 4 is a diagram showing the results of Example 4.

GST fused Smad3 or VDR (full length peptide 1–424, partial peptides: amino acid sequence 115–424, 115–357, 115–300 and others, see FIG. 4) fused proteins (GST-Smad3 or GST-VDR) were expressed by using $E.coli$, and were captured on beads with glutatione-Sepharose bead (Pharmacia) to accomplish affinity purification. On the other hand, $^{35}$S-methionine-labeled Smad3 and VDR were prepared in cell-free system by using reticulocyte lysate translation system (Promega). GST-Smad3 or GST-VDR fixed on beads described above was incubated with $^{35}$S-methionine labeled VRD or Smad3. By using polyacrylamide gel electrophoresis, $^{35}$S-methionine labeled VDR or Smad3 were analyzed.

Figure 5:
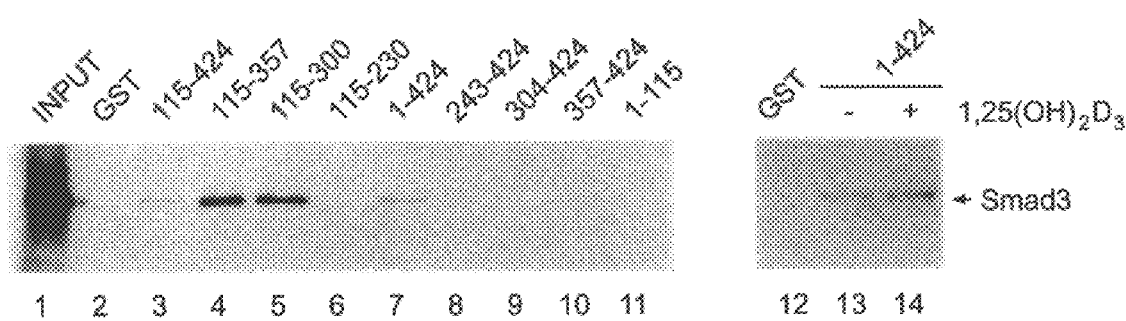
FIG. 5 is a diagram showing the results of Example 4.

The results show that VDR partial peptides, 115–357 and 115–300 bound to Smad3. This binding did not require 1,25(OH)2VD3. On the other hand, full length VDR slightly bound to Smad3 in the presence of 1 nM of 1,25(OH)2VD3 (FIG. 5).

The disjunction from the result of 1,25(OH)2VD3 in cell system is presumed that in cell system, in the presence of 1,25(OH)2VD3, intranuclear receptor transcription coupling factor (SRC-1/TIFII family protein) interacts with AF-2 core domain located near to C-terminal of VDR to result in the structure change of VDR and to make partial peptide of main central portion of VDRE domain (amino acid: 115–357, 115–300) possible to interact with (bind to) Smad molecule. In cell-free system, the strong binding of full length VDR and Smad molecule is not detected even though 1,25(OH) 2VD3 is added into the reaction system because of lacking transcription coupling factor.

Because VDR(115–300) and VDR(115–357) are VDR partial peptides containing binding site with Smad3, it is possible to screen materials accelerating or inhibiting VDR—Smad interaction (binding) by adding a material to be tested into GST-pull down analysis system using GST-VDR(115–300) or GST-VDR(115–357) and labeled Smad3.

Any analysis system other than GST-pull down method, in which interaction (binding) between proteins can be measured enables to screen materials accerelating or inhibiting the interaction of Smad molecule and intranuclear molecule. Such measurement systems are possibly ELISA, RIA, SPA method, BIACORE™, fluorescence ellipsometric method. Furthermore, respective partial peptides of Smad molecule and intranuclear receptor molecule can be used.

Moreover, respective partial peptides of Smad or intranuclear receptor molecule can be used as a fusion protein fused with tag such as FLAG-, HA-, His-, Fc portion of immunoglobulin, GST-, GFP or labeled protein/peptide.

Example 5
Detection for interaction of Smad molecule and CBP/p300
—GST-pull down method—

Figure 6A:
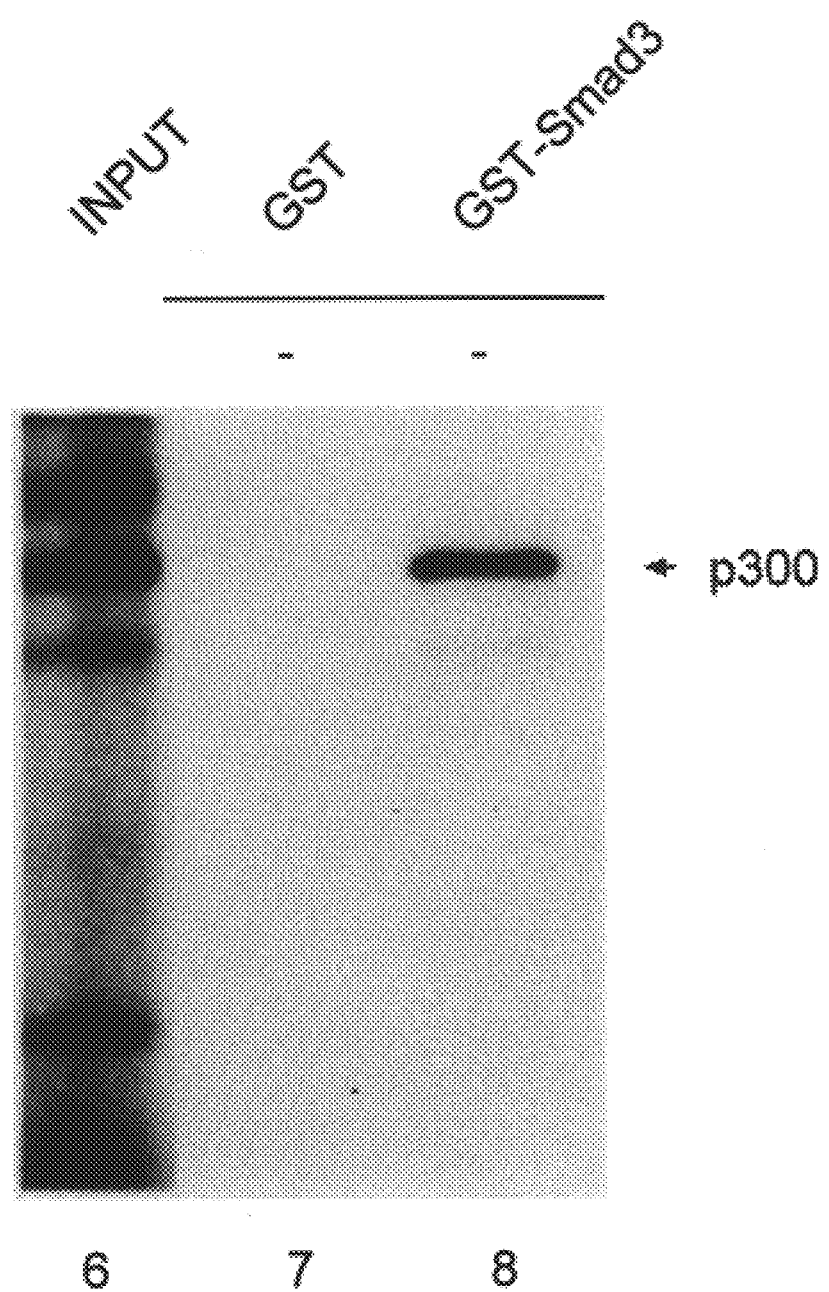
FIG. 6A is electrophoresis patterns showing the results of Example 3 in the case of p300.
Figure 6B:
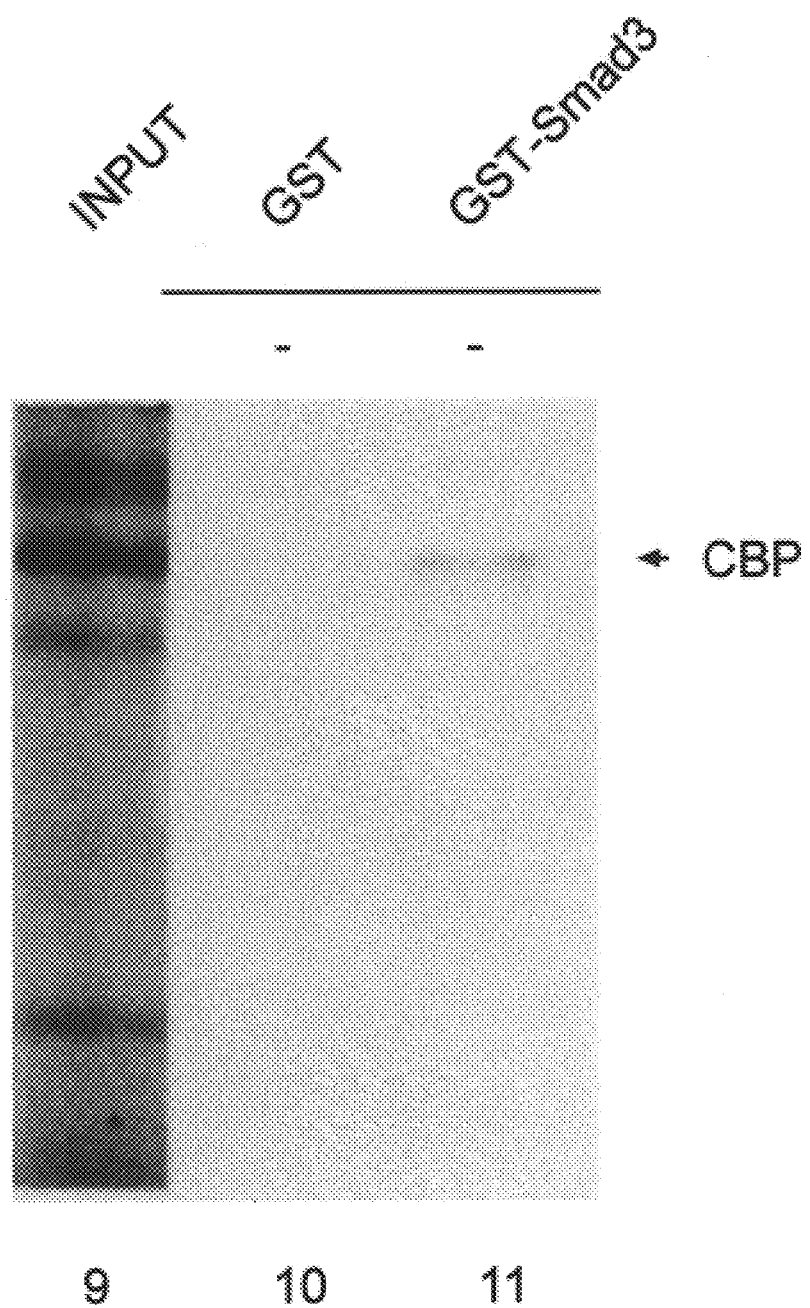
FIG. 6B is electrophoresis patterns showing the results of Example 3 in the case of CBP.

GST fused Smad3 fusion protein (GST-Smad3) was expressed by using $E.coli$, and was captured on beads with glutatione-Sepharose bead (Pharmacia) to accomplish affinity purification. On the other hand, $^{35}$S-methionine-labeled CBP and p300 were prepared in cell-free system by using reticulocyte lysate translation system (Promega). GST-Smad3 fixed on beads described above was incubated with $^{35}$S-methionine labeled CBP or p300. After accomplishing SDS-polyacrylamide gel electrophoresis, $^{35}$S-methionine labeled CBP or p300 was analyzed by using autoradiography. The results show that CBP and p300 bound to Smad3 directly (FIGS. 6A and 6B).

In this analysis system, when GST-Smad3 and $^{35}$S-methionine labeled CBP (GST-Smad3 and $^{35}$S-methlonine labeled p300) are reacted together, the resultant autoradiographical band of CBP or p300 would be increased or decreased in the presence of any material accelerating or inhibiting the binding of these molecules. By using such change as indicator, it is possible to screen materials modifying (accelerating or inhibiting) the interaction of Smad3 and CBP/p300.

As a summary, based on the novel knowledge which intracellular signal transfer mechanism from TGF-β super family by TGF-β super family stimulation do cross talk with intranuclear receptor or transcription control factor CBP/p300 via Smad molecule, a screening method for pharmaceuticals (such as inhibitor, accelerator) with high specificity can be accomplished.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method of screening for a substance that inhibits or induces interaction between an intranuclear receptor and a Smad molecule comprising the following steps:
   a. preparing a culture system consisting of introducing an intranuclear receptor expression vector and a Smad molecule expression vector into cultured cells and culturing said cells;

b. adding a substance to be tested to said culture system; and c. measuring the inhibition activity or induction activity of said substance by detecting the binding of said intranuclear receptor to said Smad molecule.

2. A method of screening for a substance as claimed in claim 1, wherein said binding of said intranuclear receptor to said Smad molecule is detected by the Two-Hybrid System.

3. A method of screening for a substance as claimed in claim 1, wherein said binding of said intranuclear receptor to said Smad molecule is detected by an antigen-antibody reaction.

4. A method of screening for a substance as claimed in claim 1, wherein said intranuclear receptor is a vitamin D receptor.

5. A method of screening for a substance as claimed in claim 1, wherein said Smad molecule is Smad3.

6. A method of screening for a substance that inhibits or induces interaction between an intranuclear receptor and a Smad molecule, by detecting interaction between an intranuclear receptor and a Smad molecule comprising:

physically contacting said intranuclear receptor with said Smad molecule in the presence or absence of a substance to be tested; detecting the binding of said intranuclear receptor to said Smad molecule; and measuring the inhibition activity or induction activity of said substance.

7. A method of screening for a substance as claimed in claim 6, wherein said binding of said intranuclear receptor to a Smad molecule is detected by GST-pull down analysis.

8. A method of screening for a substance as claimed in claim 6, wherein said binding of said intranuclear receptor to a Smad molecule is detected by a method selected from the group consisting of ELISA, RIA, SPA, BIACORE™ and fluorescence polarization methods.

* * * * *